United States Patent [19]

Kishner

[11] 4,022,534
[45] May 10, 1977

[54] REFLECTOMETER OPTICAL SYSTEM

[75] Inventor: Stanley J. Kishner, Pomona, N.Y.

[73] Assignee: Kollmorgen Corporation, Hartford, Conn.

[22] Filed: Mar. 23, 1976

[21] Appl. No.: 669,592

[52] U.S. Cl. .............................................. 356/210
[51] Int. Cl.² ..................................... G01N 21/48
[58] Field of Search ........................... 356/209, 210

[56] References Cited
UNITED STATES PATENTS

| | | | |
|---|---|---|---|
| 2,311,101 | 2/1943 | Tuttle et al. | 356/210 |
| 3,792,268 | 2/1974 | Bjerke et al. | 356/210 |
| 3,918,814 | 11/1975 | Weiser | 356/138 |

Primary Examiner—John K. Corbin
Assistant Examiner—Richard A. Rosenberger
Attorney, Agent, or Firm—Morgan, Finnegan, Pine, Foley & Lee

[57] ABSTRACT

A reflectometer optical system having an optical axis for illuminating a sample with flux derived from an extended source such as a pulsed xenon flashtube. A wedge-shaped diffuser, symmetric with respect to the optical axis, is used to diffuse the flux emanating from the source and refract it radially outward from the optical axis. The polished inner surface of a cylinder is used to reflect these radially expanding rays such that they converge upon the sample area from all azimuth angles. A series of baffles are located between the diffuser and the sample to limit the flux incident upon the sample to a small angular spread about 45°. A lens located along the optical axis focuses the flux diffusely reflected from the sample onto one end of a fiber optical bundle. An aperture stop disposed between the lens and the sample limits the reflected flux to a small angular spread about 0° while the end of the fiber optic bundle serves as a field stop to limit the region of the sample from which reflcted light is collected.

12 Claims, 1 Drawing Figure

REFLECTOMETER OPTICAL SYSTEM

BACKGROUND AND BRIEF DESCRIPTION OF THE INVENTION

A reflectometer is an optical system used to measure diffusely reflected light. Reflectometers are generally used in applications of diffuse reflectance spectroscopy. These applications cover the gamut from routine quality control testing to basic research. Reflection densitometers, for example, measure the negative logarithm of the diffuse reflectance of a sample in one of several specified sprectral bands. They are used in the measurement of such materials as photographic prints, printing ink on paper, plastic or metal substrates, and thin layer chromatograms. Reflection spectrophotometers generally measure diffuse reflectance in many narrow spectral bands for such applications as the measurement of the color of paints, plastics and textiles, and the analysis of powdered chemicals or biological specimens. The present invention relates to the illumination and collection optics for a diffuse reflectometer.

Diffuse reflectance, insofar as the preferred embodiment of the present invention is concerned, is defined as the ratio of light flux reflected normal to a sample to the light flux diffusely incident upon it. Diffuse reflectance can also be defined in terms of normal illumination and diffuse collection.

Thus, a diffuse reflectance measurement excludes specular reflections. Diffuse illumination is usually provided in one of two forms--sphere illumination or 45° illumination. In sphere illumination the illumination comes from an integrating sphere and is incident upon the sample from all directions (in a hemisphere). In 45° illumination the incident light is concentrated in an annulus that impinges at 45° to the sample, with a slight angular spread about 45°. The diffusely reflected light is collected normal to the sample, with a slight angular spread about the normal. This illumination/collection geometry is commonly called 45°/0° and is the subject of the preferred embodiment of the present invention.

The illumination optics provide illumination from a complete annular ring, the rays of such illumination having an angle of incidence lying in a prescribed angular spread about 45° to the sample normal. Furthermore, the illumination incident upon the sample is of uniform irradiance over a prescribed circular region of the sample. The collection optics receive light that is diffusely reflected from the sample in a cone of prescribed half-angle about the sample normal. It furthermore restricts such collection to the same circular region of the sample that has been uniformly illuminated. The collection optics also provide for spectral filtering of the reflected light and can direct this light via an optical fiber to a photodetector in a remote location.

The entire optical system is comprised of elements that are relatively simple to manufacture or readily available at low cost and does not involve the use of any high quality optical elements. There is no restriction on the size of the optical system so that it can be used for making diffuse reflectance measurements on small or large area samples, whether stationary or moving, and need not contact the sample. In addition, the optical system meets the geometrical conditions specified by the American National Standards Institute for diffuse reflectance measurements on photographic and graphic arts materials.

BRIEF DESCRIPTION OF THE DRAWINGS

The above as well as other objects of the invention will become apparent from a consideration of the following description taken in conjunction with the accompanying drawings in which.

DETAILED DESCRIPTION

Figure 1:
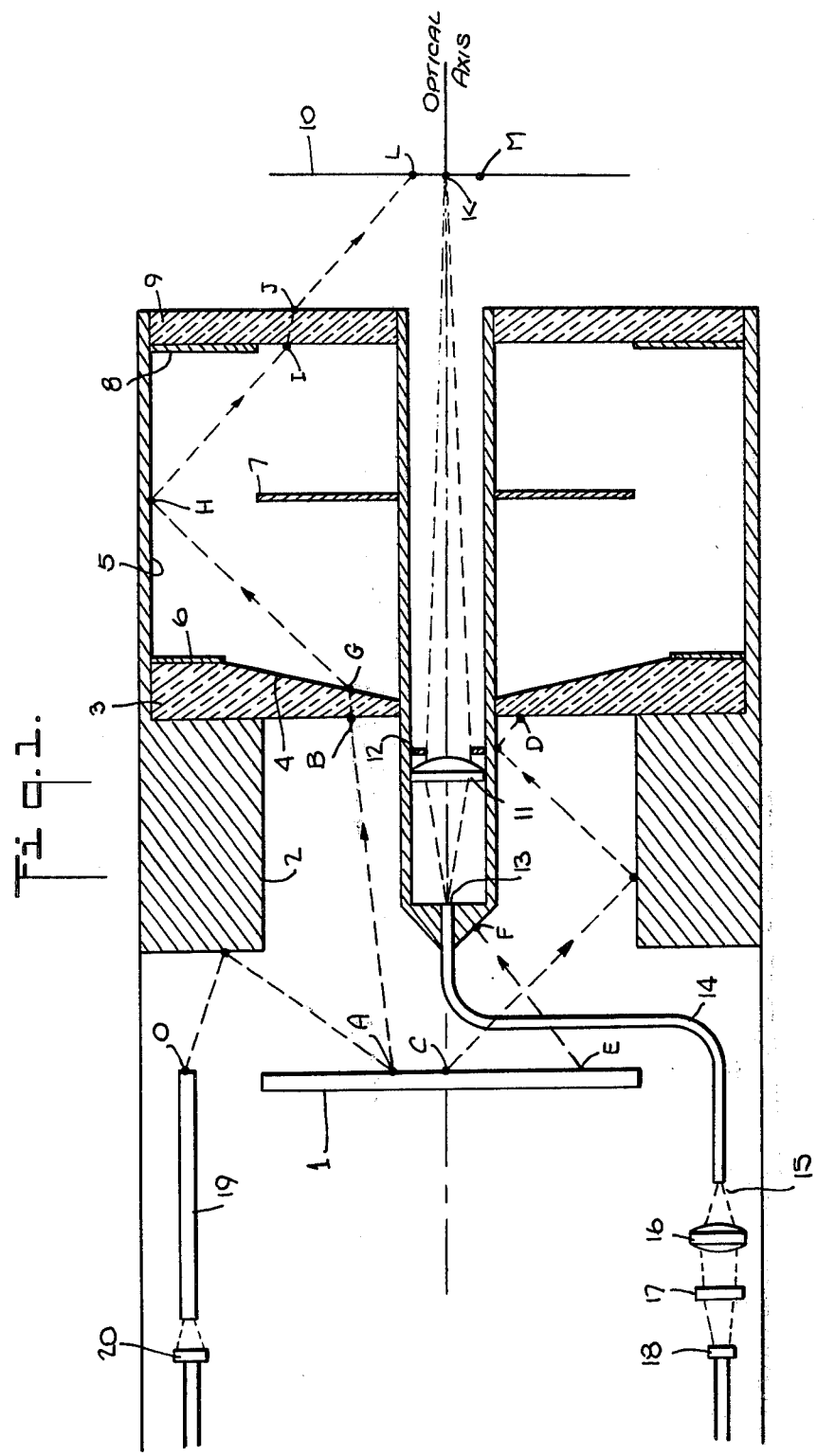
FIG. 1 is a view in section of the illumination and collection optics of a reflectometer.

Referring now to FIG. 1, it should first be noted that all system components are circularly symmetric about the optical axis of the system, with the exception of source 1 and elements 14 through 20 of the collection optics.

Light source 1 is an extended source, preferably the arc from a pulsed xenon flashtube. Light flux from the source that is incident upon the circular aperture defined by the cylindrical surface 2 impinges upon a glass or plastic circular wedge 3 either directly, as shown by ray AB, or via one or more reflections, as shown by ray CD. The surface of the cylinder 2 is polished in order to maximize its reflectivity. Some rays from the source, such as ray EF, do not reach the circular wedge 3 because they first impinge on portions of the collection optical system.

The wedged surface 4 serves to refract incident rays in a direction radially outward from the optical axis. For example, ray AB is refracted outward at G towards H. The surface 4 need not be conical as shown, as long as it serves to refract rays radially outward. Such refraction will occur if surface 4 is designed such that the wedge thickness increases with radius. For example, a concave surface would achieve the desired end. The wedged surface 4 is ground in order to diffuse the light passing through it. The purpose of this diffuser is to provide uniform illumination of the sample. Without the diffuser, the irradiance at the sample would be structured and therefore quite nonuniform.

After being refracted and diffused, the light flux is reflected from a polished cylindrical surface 5 such that it is directed radially inward at angles at and around 45°. Surface 5 need not be an annular section of a cylindrical surface as shown, as long as it reflects rays that are incident from the wedge radially inward at 45°. Thus, if rays are incident from the wedge at angles other than 45°, an annular section of a conical surface could be used to achieve the desired end. Also, an annular section from an ellipsoid could be used. In applications where it is acceptable for the rays incident on the sample to be at angles other than 45°, any of the above annular reflectors could be designed for such use. Opaque baffles 6, 7 and 8 block any rays that can impinge on the sample at angles outside the prescribed angular spread about 45°. A clear glass disk 9 is used as a protective window. After passing through this disk, the light flux impinges on the sample 10 from a complete 360° annulus and at angles at and about 45° from the sample normal. Because of diffuser 4, the illumination is uniform over a prescribed circular area defined by points L and M.

Light flux that is diffusely reflected from the sample is collected by lens 11 in a cone of prescribed half-angle, centered about the sample normal. The half-angle is defined by an aperture stop 12 placed before lens 11, or by the lens itself in the absence of an aperture stop. The circular region of the sample as defined by points L and M is imaged by lens 11 onto the end 13 of a fiber optic bundle 14. The end of the bundle serves as a field stop, strictly defining the region on the sample from which light is collected. Thus, the lens demagnifies the sample region so that is image is exactly the same size as the end of the fiber optic bundle 13. If a smaller auxiliary stop were placed in front of the fiber, the sample region would be reduced further.

The fiber optic bundle can be bent over a relatively small radius of curvature and is therefore bent out of the way of source 1. It directs the light incident on its end 13 along its length and out its other end 15. The light flux emanating from the fiber is focused by lens 16, preferably a glass sphere, through a spectral filter 17 onto photodetector 18, which may be a silicon photodiode. Fiber optic bundle 14 can be quite long, so that the photodetector can be located remote from the collection optics if desired.

The spectral filter is preferably an interference filter with a half bandwidth of about 10–20nm and is chosen at a wavelength corresponding to the absorption maximum of the sample being measured. The use of narrowband filters, rather than broader gelatin filters, increases the sensitivity to small variations in color. The spectral filter may be a single filter or a filter wheel that provides a choice of several such filters.

A reference channel comprising fiber optic bundle 19 and photodetector 20 is also provided. A small sample of the radiation emitted by source 1 is collected by fiber optic bundle 19, for example from ray AO. Fiber otpic bundle 19 transmits this sample of the source radiation to photodetector 20 where it is converted to an electrical signal.

The invention disclosed and claimed herein is not limited to the specific mechanism and techniques herein shown and described since modifications will undoubtedly occur to those skilled in the art. Hence, departures may be made from the form of the instant invention without departing from the principles thereof.

What I claim is:

1. A reflectometer optical system having an optical aixs for illuminating a sample with flux derived from an extended source comprising:
   a. a diffuser radially symmetric with respect to said optical axis and responsive to flux emanating from said source for diffusing said flux and refracting it radially outward from said optical axis;
   b. a reflective surface intermediate said diffuser and said sample for reflecting said flux diffused by said diffuser, said reflective surface being radially symmetric with respect to said optical axis;
   c. a plurality of baffles disposed between said diffuser and said sample for limiting said flux incident upon said sample to a small angular spread about 45°;
   d. means located on said optical axis for focusing the flux reflected from said sample and for limiting said reflected flux to a small angular spread about 0°; and
   e. a fiber optic bundle for receiving and transmitting the reflected flux focused by said means.

2. A reflectometer optical system according to claim 1 further including:
   a. a lens for receiving and focusing reflected flux transmitted by said fiber optic bundle; and
   b. a spectral filter for filtering the reflected flux focused by said second lens.

3. A reflectometer optical system according to claim 1 further including:
   a. a spherical lens for receiving and focusing said reflected flux transmitted by said fiber optic bundle; and
   b. an interference filter having a half bandwidth of about 10–20nm, chosen at a wavelength corresponding to the absorption maximum of the sample being measured, for filtering the reflected flux focused by said spherical lens.

4. A reflectometer optical system according to claim 3 wherein said diffuser is wedge-shaped and said reflective surface is cylindrical.

5. A reflectometer optical system according to claim 1 wherein said diffuser is wedge-shaped.

6. A reflectometer optical system according to claim 1 wherein said reflective surface is cylindrical.

7. A reflectometer optical system according to claim 1 wherein the end of said fiber optic bundle serves as a field stop to further define the region on the sample from which the reflected flux is collected.

8. A reflectometer optical system according to claim 1 wherein said diffuser is wedge-shaped and said reflective surface is cylindrical.

9. A reflectometer optical system having an optical axis for illuminating a sample with flux derived from an extended source comprising:
   a. a diffuser symmetric with respect to said optical axis and responsive to flux emanating from said source for diffusing said flux and refracting it radially outward from said optical axis;
   b. a reflective surface intermediate said diffuser and said sample for reflecting said flux diffused by said diffuser, said reflective surface being radially symmetric with respect to said optical axis;
   c. a plurality of baffles disposed between said diffuser and said sample for limiting said flux incident upon said sample to a small angular spread about 45°;
   d. a lens located on said optical axis for focusing the flux reflected from said sample;
   e. an aperture stop located on said optical axis between said sample and said lens for limiting said reflected flux to a small angular spread about 0°; and
   f. a fiber optic bundle for receiving and transmitting the reflected flux focused by said lens, the end of said fiber optic bundle serving as a field stop to further define the region on the sample from which reflected flux is collected.

10. A reflectometer optical system according to claim 9 further including:
    a. a second lens for receiving and focusing said reflected flux transmitted by said fiber optic bundle; and
    b. an interference filter for filtering the reflected flux focused by said lens.

11. A reflectometer optical system according to claim 10 further including a reference channel comprising a second fiber optic bundle having one end located proximate said source for receiving and transmitting a portion of said flux emanating from said source.

12. A reflectometer optical system according to claim 11 wherein said diffuser is wedge-shaped and said reflective surface is cylindrical.

* * * * *